(12) United States Patent
Friedlander et al.

(10) Patent No.: US 8,655,681 B2
(45) Date of Patent: Feb. 18, 2014

(54) COHORT DRIVEN SELECTION OF MEDICAL DIAGNOSTIC TESTS

(71) Applicant: International Business Machines Corporation, Armonk, NY (US)

(72) Inventors: Robert R. Friedlander, Southbury, CT (US); James R. Kraemer, Santa Fe, NM (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 13/939,620

(22) Filed: Jul. 11, 2013

(65) Prior Publication Data

US 2013/0304494 A1 Nov. 14, 2013

Related U.S. Application Data

(63) Continuation of application No. 13/158,858, filed on Jun. 13, 2011.

(51) Int. Cl.
*G06Q 10/00* (2012.01)

(52) U.S. Cl.
USPC .............................................. 705/2; 707/752

(58) Field of Classification Search
USPC .............................................. 705/2; 128/923
IPC .............................................. A61B 5/00,10/00
See application file for complete search history.

(56) References Cited

U.S. PATENT DOCUMENTS

| 5,551,436 | A | 9/1996 | Yago |
| 7,580,922 | B2 | 8/2009 | Friedlander et al. |
| 7,761,440 | B2 | 7/2010 | Chow et al. |
| 7,788,202 | B2 | 8/2010 | Friedlander et al. |
| 7,805,391 | B2 | 9/2010 | Friedlander et al. |
| 7,809,660 | B2 | 10/2010 | Friedlander et al. |
| 2002/0062226 | A1 | 5/2002 | Ito et al. |
| 2006/0200010 | A1 | 9/2006 | Rosales et al. |

(Continued)

FOREIGN PATENT DOCUMENTS

| JP | 2010-017519 | 1/2010 |
| WO | 2009103156 A1 | 8/2009 |

OTHER PUBLICATIONS

Guide to History Taking and Examination, Oct. 2009, University College London Medical School, p. 2-9.*

(Continued)

*Primary Examiner* — John Pauls
*Assistant Examiner* — Jason Tiedeman
(74) *Attorney, Agent, or Firm* — John R. Pivnichny; Law Office of Jim Boice

(57) ABSTRACT

A computer implemented method, system, and/or computer program product creates a suggested diagnostic test selection. A description of a current patient includes a current medical complaint, medical history, and physical examination result for the current patient. A cohort for the current patient is made up of persons who have a substantially similar medical complaint, medical history, and physical examination result as the current patient. Past diagnostic test sets used to make correct medical diagnoses for persons in the cohort are identified and stored in a cohort diagnostic test database. The past diagnostic test sets are sorted based on increasing levels of detrimental effects posed by each of the past diagnostic test sets. The sorted diagnostic test sets are then presented to a health care provider for the current patient.

20 Claims, 6 Drawing Sheets

(56) References Cited

U.S. PATENT DOCUMENTS

| | | | |
|---|---|---|---|
| 2007/0143035 A1* | 6/2007 | Petruno | 702/27 |
| 2007/0276777 A1 | 11/2007 | Krishnan et al. | |
| 2009/0094063 A1* | 4/2009 | Ennett | 705/3 |
| 2009/0177645 A1 | 7/2009 | Heck | |
| 2009/0240523 A1 | 9/2009 | Friedlander et al. | |
| 2009/0259494 A1* | 10/2009 | Feder et al. | 705/3 |
| 2009/0299766 A1* | 12/2009 | Friedlander et al. | 705/3 |
| 2010/0010316 A1 | 1/2010 | Fueyo et al. | |
| 2010/0010363 A1 | 1/2010 | Fueyo et al. | |
| 2010/0010827 A1 | 1/2010 | Fueyo et al. | |
| 2010/0152885 A1 | 6/2010 | Regan et al. | |
| 2010/0241472 A1* | 9/2010 | Hernandez | 705/7 |
| 2010/0251117 A1 | 9/2010 | Baughman et al. | |
| 2011/0060737 A1* | 3/2011 | Cardella | 707/732 |
| 2012/0265550 A1 | 10/2012 | Friedlander et al. | |
| 2012/0316891 A1 | 12/2012 | Friedlander et al. | |
| 2012/0317127 A1 | 12/2012 | Friedlander et al. | |

OTHER PUBLICATIONS

Pettitt et al., Comparison of World Hearth Organization and National Diabetes Data Group Procedures to Detect Abnorillalities of Glucose Tolerance During Pregnancy, Nov. 1994, Diabetes Care, vol. 17, No. 11, p. 1264-66.*

U.S. Appl. No. 13/159,076, Robert R. Friedlander et al.—Non-Final Office Action Mailed November 29, 2012.

U.S. Appl. No. 13/086,539, Robert R. Friedlander et al.—Non-Final Office Action Mailed November 9, 2012.

U.S. Appl. No. 13/086,539—Final Office Action Mailed April 26, 2013.

Anonymous, "Attributable", vocabulary.com, Apr. 2013, pp. 1.

Owen Bond, "Tinnitus and Vitamin Deficiencies", livestrong.com, Apr. 16, 2011, pp. 1-3.

U.S. Appl. No. 13/159,076—Final Office Action Mailed May 10, 2013.

Fundakowski et al, "Disfigurement Perception, Quality of Life, and Mental Health in the Post-Treatment Head and Neck Cancer Patient", University of Miami—Miller School of Medicine, N.D., pp. 1. Jan. 2012.

Anonymous, "Loss of Mobility Found to Impact Quality of Life and Emotional and Financial Health of Most People Living With Multiple Sclerosis," Acorda Therapeutics, Inc., Mar. 25, 2008, pp. 1-4.

Hertenstein et al., "Quality of Life Changes Following Inpatient and Outpatient Treatment in Obsessive-Compulsive Disorder: A Study With 12 Months Follow-Up," Annals of General Psychiatry, 2013, 12:4, pp. 1-9.

Katz, "The Impact of Pain Management on Quality of Life", Proceedings From the Roundtable on "The Role of Coxibs in Successful Pain Management", Journal of Pain and Symptom Management, vol. 24, No. 15, Jul. 2002, pp. S38-S47.

Anonymous, "Treat", dictionary.com, Apr. 2013, pp. 1-3.

Ziaian et al., "Treatment Burden and Health-Related Quality of Life of Children With Diabetes, Cystic Fibrosis and Asthma", Journal of Paediatrics and Child Health 42, 2006, pp. 596-600.

Pettitt et al., "Comparison of World Health Organization and National Diabetes Data Group Procedures to Detect Abnormalities of Glucose Tolerance During Pregnancy", Diabetes Care, vol. 17, No. 11, Nov. 1994, pp. 1264-1266.

U.S. Appl. No. 13/158,858, Robert R. Friedlander et al., Non-Final Office Action Mailed Nov. 21, 2012.

Anonymous, "Guide to History Taking and Examination", University College London Medical School, Oct. 2009, pp. 1-40.

U.S. Appl. No. 13/086,539—Notice of Allowance Mailed November 25, 2013.

U.S. Appl. No. 13/159,076—Examiner'S Answer Mailed Dec. 9, 2013.

* cited by examiner

COHORT DRIVEN SELECTION OF MEDICAL DIAGNOSTIC TESTS

The present application is a continuation of U.S. patent application Ser. No. 13/158,858, filed on Jun. 13, 2011, and entitled, "Cohort Driven Selection of Medical Diagnostic Tests," which is incorporated herein by reference.

BACKGROUND

The present disclosure relates to the field of computers, and specifically to the use of computers in the field of medicine. Still more particularly, the present disclosure relates to the use of computers in choosing diagnostic tests.

Selecting which medical diagnostic tests to administer to a patient is often an inexact science. That is, symptoms presented by a patient via the patient's complaints and physical appearance may suggest several different underlying medical issues or concerns. Confirmation of the presence of one of these different suggested underlying diseases often requires the administration of disease-specific diagnostic tests. If an administered diagnostic test turns out to be incorrect for the patient's malady, then time, money, and resources are wasted.

SUMMARY

A method, system, and/or computer program product creates a suggested diagnostic test selection. A description of a current patient includes a current medical complaint, medical history, and physical examination result for the current patient. A cohort for the current patient is made up of persons who have had a substantially similar medical complaint, medical history, and physical examination result as the current patient. Past diagnostic test sets used to make correct medical diagnoses for persons in the cohort are identified and stored in a cohort diagnostic test database. The past diagnostic test sets are sorted based on increasing levels of detrimental effects posed by each of the past diagnostic test sets. The sorted diagnostic test sets are then presented to a health care provider for the current patient.

DETAILED DESCRIPTION

Figure 1:
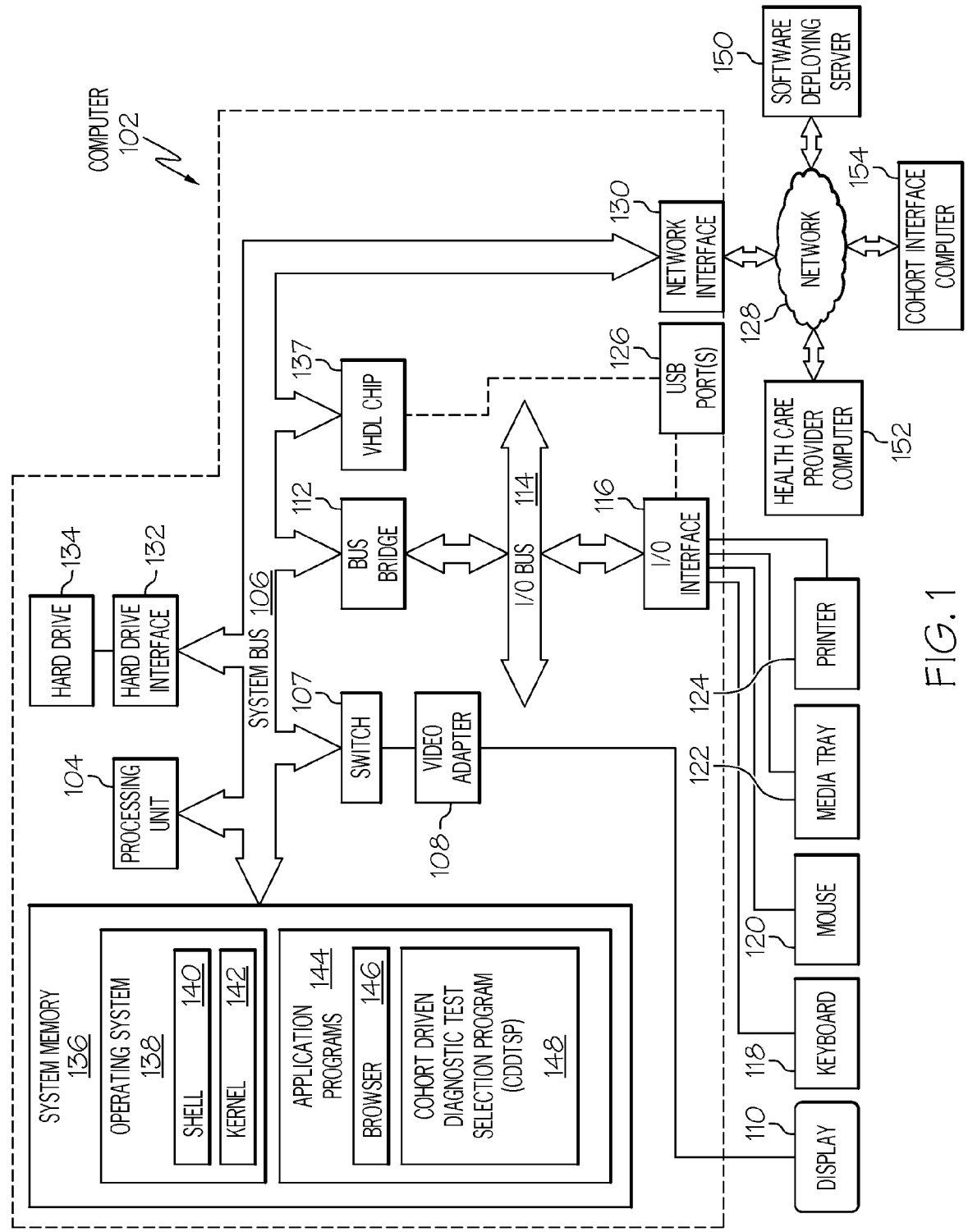
FIG. 1 depicts an exemplary computer in which the present disclosure may be implemented.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including, but not limited to, wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

With reference now to the figures, and in particular to FIG. 1, there is depicted a block diagram of an exemplary computer 102, which may be utilized by the present invention. Note that some or all of the exemplary architecture, including both depicted hardware and software, shown for and within computer 102 may be utilized by software deploying server 150, a health care provider computer 152, and/or a cohort interface computer 154.

Computer 102 includes a processing unit 104 that is coupled to a system bus 106. Processing unit 104 may utilize one or more processors, each of which has one or more processor cores. A video adapter 108, which drives/supports a display 110, is also coupled to system bus 106. System bus 106 is coupled via a bus bridge 112 to an input/output (I/O) bus 114. An I/O interface 116 is coupled to I/O bus 114. I/O interface 116 affords communication with various I/O devices, including a keyboard 118, a mouse 120, a media tray 122 (which may include storage devices such as CD-ROM drives, multi-media interfaces, etc.), a printer 124, and external USB port(s) 126. While the format of the ports connected to I/O interface 116 may be any known to those skilled in the art of computer architecture, in one embodiment some or all of these ports are universal serial bus (USB) ports.

As depicted, computer 102 is able to communicate with a software deploying server 150 using a network interface 130. Network 128 may be an external network such as the Internet, or an internal network such as an Ethernet or a virtual private network (VPN).

A hard drive interface 132 is also coupled to system bus 106. Hard drive interface 132 interfaces with a hard drive 134. In one embodiment, hard drive 134 populates a system memory 136, which is also coupled to system bus 106. System memory is defined as a lowest level of volatile memory in computer 102. This volatile memory includes additional higher levels of volatile memory (not shown), including, but not limited to, cache memory, registers and buffers. Data that populates system memory 136 includes computer 102's operating system (OS) 138 and application programs 144.

OS 138 includes a shell 140, for providing transparent user access to resources such as application programs 144. Generally, shell 140 is a program that provides an interpreter and an interface between the user and the operating system. More specifically, shell 140 executes commands that are entered into a command line user interface or from a file. Thus, shell 140, also called a command processor, is generally the highest level of the operating system software hierarchy and serves as a command interpreter. The shell provides a system prompt, interprets commands entered by keyboard, mouse, or other user input media, and sends the interpreted command(s) to the appropriate lower levels of the operating system (e.g., a kernel 142) for processing. Note that while shell 140 is a text-based, line-oriented user interface, the present invention will equally well support other user interface modes, such as graphical, voice, gestural, etc.

As depicted, OS 138 also includes kernel 142, which includes lower levels of functionality for OS 138, including providing essential services required by other parts of OS 138 and application programs 144, including memory management, process and task management, disk management, and mouse and keyboard management.

Application programs 144 include a renderer, shown in exemplary manner as a browser 146. Browser 146 includes program modules and instructions enabling a world wide web (WWW) client (i.e., computer 102) to send and receive network messages to the Internet using hypertext transfer protocol (HTTP) messaging, thus enabling communication with software deploying server 150 and other computer systems.

Application programs 144 in computer 102's system memory (and, in one embodiment, software deploying server 150's system memory, health care provider's computer 152) also include a cohort driven diagnostic test selection program (CDDTSP) 148. CDDTSP 148 includes code for implementing the processes described below, including those described in FIGS. 2-6. In one embodiment, computer 102 is able to download CDDTSP 148 from software deploying server 150, including in an on-demand basis, wherein the code in CDDTSP 148 is not downloaded until needed for execution to define and/or implement the improved enterprise architecture described herein. Note further that, in one embodiment of the present invention, software deploying server 150 performs all of the functions associated with the present invention (including execution of CDDTSP 148), thus freeing computer 102 from having to use its own internal computing resources to execute CDDTSP 148.

The hardware elements depicted in computer 102 are not intended to be exhaustive, but rather are representative to highlight essential components required by the present invention. For instance, computer 102 may include alternate memory storage devices such as magnetic cassettes, digital versatile disks (DVDs), Bernoulli cartridges, and the like. These and other variations are intended to be within the spirit and scope of the present invention.

Note that, in one embodiment, various combinations of computer 102, health care provider computer 152, and/or cohort interface computer 154 and their functions may be integrated into one or more computers.

Note that while FIG. 1 presents a general architecture of one computing system that may be utilized in one embodiment of the present invention, in another embodiment many processing systems are utilized in parallel. In one such embodiment, these parallel computing systems directly and precisely answer natural language questions over an open and broad range of knowledge identified by Question/Answer (QA) technology that utilizes Natural Language Processing, Information Retrieval, Knowledge Representation and Reasoning, and Machine Learning technologies. This QA technology incorporates hypothesis generation, massive evidence gathering, analysis, and scoring to create an Artificial Intelligence (AI) that allows for a natural QA interaction between a health care provider and the technology described herein. This natural interaction allows the parallel computing systems to deliver precise, meaningful responses, and to synthesize, integrate, and rapidly reason in natural language text.

Figure 2:
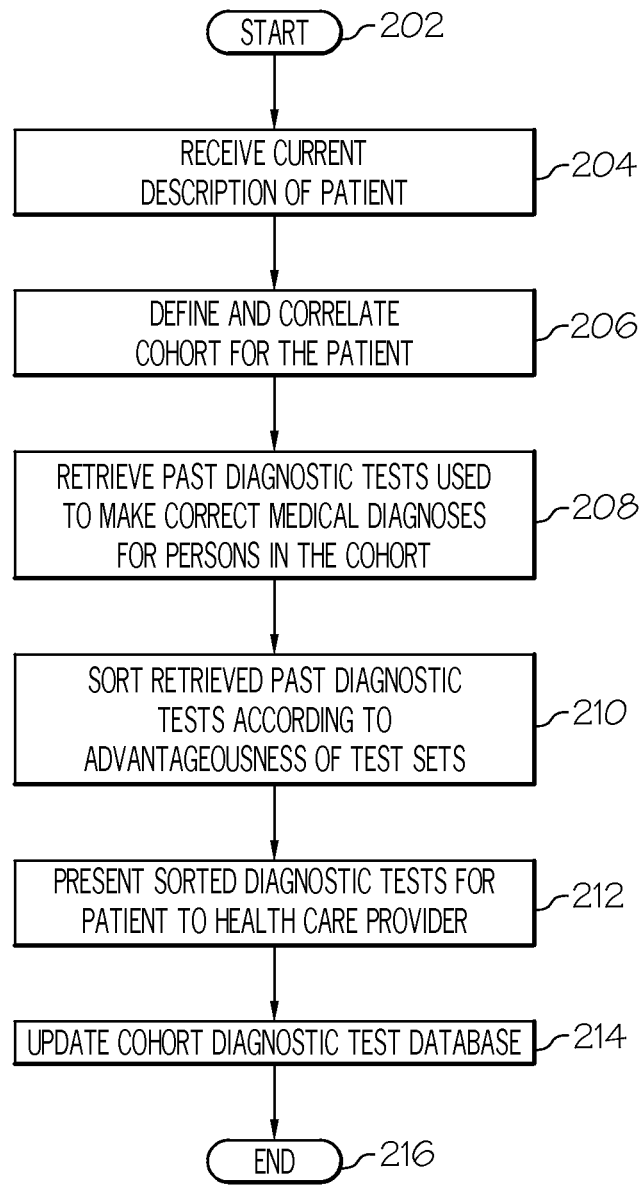
FIG. 2 is a high level flow chart of one or more exemplary steps performed by a processor to determine an optimal sequence for administering diagnostic tests for a patient.

With reference now to FIG. 2, a high level flow chart of one or more exemplary steps performed by a processor to create and suggest a course of medical diagnostic testing for a patient is presented. After initiator block 202, a current description of a patient is received by a computer, such as computer 102 depicted in FIG. 1, from a computer such as the health care provider computer 152 (also shown in FIG. 1), as described in block 204. In one embodiment, this current description includes, but is not necessarily limited to, a current complaint of the patient (i.e., what discomfort, limitations, medical anomalies are being disclosed by the patient); a medical history of the patient (i.e., a history of past medical conditions, lab test results, examination results, etc.), a current physical examination result (e.g., complaints voiced by the patient, observations made by the health care provider, etc.) for the patient, a demographic description (e.g., age, occupation, location of current residence, current income level, etc.) of the patient, a travel history (e.g., when and where the patient has traveled during some predefined period of time) of the patient; and/or any experienced traumas by the patient that are non-attributable to the current complaint of the patient (e.g., the patient may have recently broke a bone in her arm, yet is complaining of tinnitus, which is non-attributable to the broken arm).

Note that in one embodiment the medical history of patients (i.e., the current patient as well as those patients represented in a cohort database) includes previous treatments for prior conditions. Examples of such treatments for prior conditions include, but are not limited to, surgery, chemotherapy for cancer, radiation treatment for cancer, heart bypass surgery, pharmaceutical regimens, etc. Examples of non-treatment exposures include, but are not limited to, traumatic brain injury due to exposure to severe force (i.e., an open or closed head injury from an explosion), exposure to a chemical agent, which may or may not have resulted in an obstructive pulmonary disease, etc. In the prior art, such treatments and/or exposures prevent persons from participating in pharmaceutical trials and different research protocols, and thus would not be included in a cohort. However, in one embodiment of the present invention, this cumulative history of insults to the body and their associated treatment are precisely what defines the cohort, such that there is an inclusion of as many of these people as possible. Thus, while prior art cohorts are defined as a limited group according to a certain pre-defined medical condition, the present application defines a cohort as a group of persons that share a wide range of adverse, cumulative, and multiplicative features that match the current patient. In one embodiment, these features are a combination of common complaints, diagnoses, treatments, injuries, demographics, travel history, unrelated trauma, and etc. found for members of the cohort (as well as the current patient).

As described in block 206, a processor then defines/retrieves/matches the patient to a particular cohort. This cohort is made up of persons who each have a substantially similar physical examination result, demographic description, travel history, etc. as the patient. For example, assume that a database (not shown) for a group (cohort) of 100 persons is found in a system such as the cohort access computer 154 shown in FIG. 1. This database reveals that every member of this cohort has, within a predefined range, a substantially similar physical examination result, demographic description, travel history, etc. as the patient. It is this substantial similarity that places these 100 persons into the cohort.

As described in block 208, the processor then retrieves, from the cohort database (e.g., a cohort diagnostic test database presented via the cohort interface computer 154 shown in FIG. 1) past medical diagnostic tests that have accurately determined correct medical diagnoses for persons in the cohort. In one embodiment, these medical diagnostic tests produced a single diagnosis that was accurate for all members of the cohort. In another embodiment, these medical diagnostic tests produced multiple medical diagnoses, rather than a single diagnosis, for some or all members of the cohort. These past medical diagnostic tests, known as past diagnostic test sets, are sorted based on increasing levels of detrimental effects posed by each of the past diagnostic test sets (block 210). In one embodiment, these detrimental effects are the result of a delay in obtaining results from a particular diagnostic test set.

Figure 3:
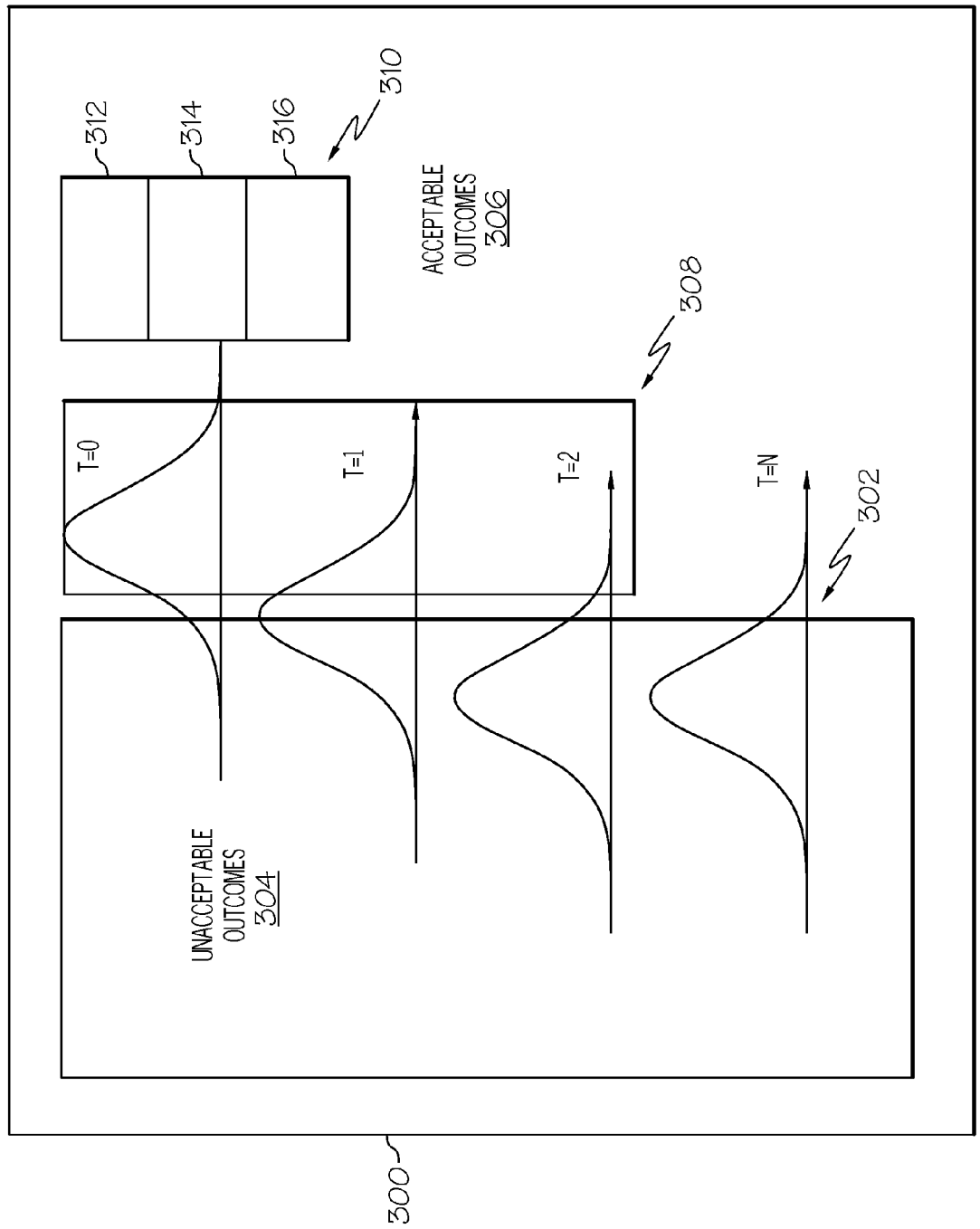
FIG. 3 is a chart depicting multiple alternative diagnostic tests that have various acceptable/unacceptable outcome levels.

For example, consider graph 300 depicted in FIG. 3. A disease is repeatedly depicted at times T0-TN as a curve 302. While the curve 302 is shown as a symmetrical curve, in one embodiment curve 302 is actually asymmetrical, indicating asymmetrical distributions of unacceptable outcomes 304 and acceptable outcomes 306. Note that an outcome is deemed unacceptable if the results meet some predefined criteria for that patient, disease, etc. Examples of such predefined criteria include the expiration of the patient, an inordinate level of disablement, an inordinate level of pain, the inability to provide additional treatment, and irreversible conditions. An inordinate level of disablement or pain is that level that goes beyond normal disablement/pain that is typically associated with a particular medical condition. An example of an inability to provide addition treatment is a surgical procedure that, if done improperly the first time due to an incorrect diagnosis/test, cannot be redone (or undone) later. Another example of the inability to provide additional treatment is the administration of certain pharmaceuticals, which if improper/ineffective, nonetheless preclude, for pharmacological reasons, administering other pharmaceuticals. An irreversible condition is similar to an inability to provide addition treatment. An example of such an irreversible condition is incorrectly removing a misdiagnosed and yet healthy organ, limb, etc.

In one embodiment, an outcome may be deemed unacceptable, even if reversible, if the cost to correct the outcome is greater than a permissible upper limit. This cost may be monetary, physical (i.e., correcting the problem will cause and/or exacerbate other medical conditions of the patient), emotional (i.e., correcting the problem will cause unacceptable levels of stress on the patient and/or the patient's family), etc.

Note that the sorting of the various diagnostic test sets described in block 210 of FIG. 2 may be based on various detrimental effects to the patient. For example, the detrimental effects may occur due to a delay in obtaining results from a particular diagnostic test set, as described in FIG. 3, and discussed in detail below. However, other detrimental effects to the general population and/or to members of the cohort described herein may include excessive cost (above a certain predetermined level, not covered by insurance, etc.) of a particular diagnostic test set, excessive pain inflicted on the patient from the particular diagnostic test set, irreversible conditions that will (or may) be inflicted on the patient as a result of simply administering the particular diagnostic test set, etc.

An acceptable outcome 306 is an outcome in which the patient suffers pain, cost, disablement, etc. that are all below a predefined threshold.

As depicted in FIG. 3, at time T0 (i.e., when the patient first presents himself to a health care provider/facility), 93% of the time the patient having the disease depicted in graphs 302 suffers no unacceptable outcomes 304 (i.e., there is no immediate adverse impact on the patient from the disease that is afflicting the patient if proper treatment begins immediately or, in some cases, even if no treatment is given), while 7% of the time the patient will suffer adverse effects from the disease even if treatment does begin immediately. At time T1, which is a predefined time period that may be minutes, hours, days, weeks, months, or even years after time T0, the treated disease results in unacceptable results/outcomes 45% of the time. This high level of unacceptable results/outcomes is due to the fact that the treatment came too late to provide optimal results. After time T2, the unacceptable results/outcomes occur 90% of the time, even though appropriate treatment for the diagnosed disease is given to the patient at time T2. In the example depicted in FIG. 3, the detrimental effects of the disease described by graph 302 plateau after time T2, such that there are no additional detrimental effects at later times (e.g., time TN). That is, in 10% of the time the disease causes only acceptable outcomes 306, even if treatment is unduly delayed and/or withheld entirely.

As thus described in FIG. 3, the detrimental effect of a particular diagnostic test set (or one or more tests) may be a delay in receiving test results from that particular diagnostic test set. Thus, a certain (i.e., 100% accurate) diagnosis can be reached by performing a diagnostic test depicted by block 308. However, this diagnostic test takes until time T2 for the test results to be returned, at which time the patient will likely suffer an unacceptable outcome even if appropriate treatment is give (at time T2). However, an alternative diagnostic test, represented by block 310, may be given. This alternative diagnostic test takes only until time T1 for results to be returned, thus giving the patient a better chance of an acceptable outcome as compared to waiting for the result of the test depicted by block 308. However, the accuracy of the diagnostic test for all patients may only be 60%, which would ordinarily be too low to justify treatment of the diagnosed disease. In accordance with the present invention, however, an examination of persons in the cohort who have the same traits as the current patient may reveal that this test was 95% accurate when administered to these persons. Thus, the health care provider can be much more confident in the test results given by the diagnostic test depicted by block 310. Therefore, the diagnostic test represented by block 310 has a lower detrimental effect level (due to the patient being able to timely receive proper treatment) than the diagnostic test represented by block 308, and also allows the patient to receive more timely treatment. Thus, sorting of these two diagnostic tests will rank the diagnostic test represented by block 310 higher than the diagnostic test represented by block 308.

As depicted in FIG. 3, the diagnostic test represented by block 310 may be made up of a single diagnostic test (i.e., a set of one), or block 310 may be made up of multiple sequential diagnostic tests (i.e., a multiple set), in which the diagnostic test represented by block 316 is performed after the diagnostic test represented by block 314 (i.e., depending on the results of the diagnostic test represented by block 314), which is performed after the diagnostic test represented by block 312.

Figure 4:
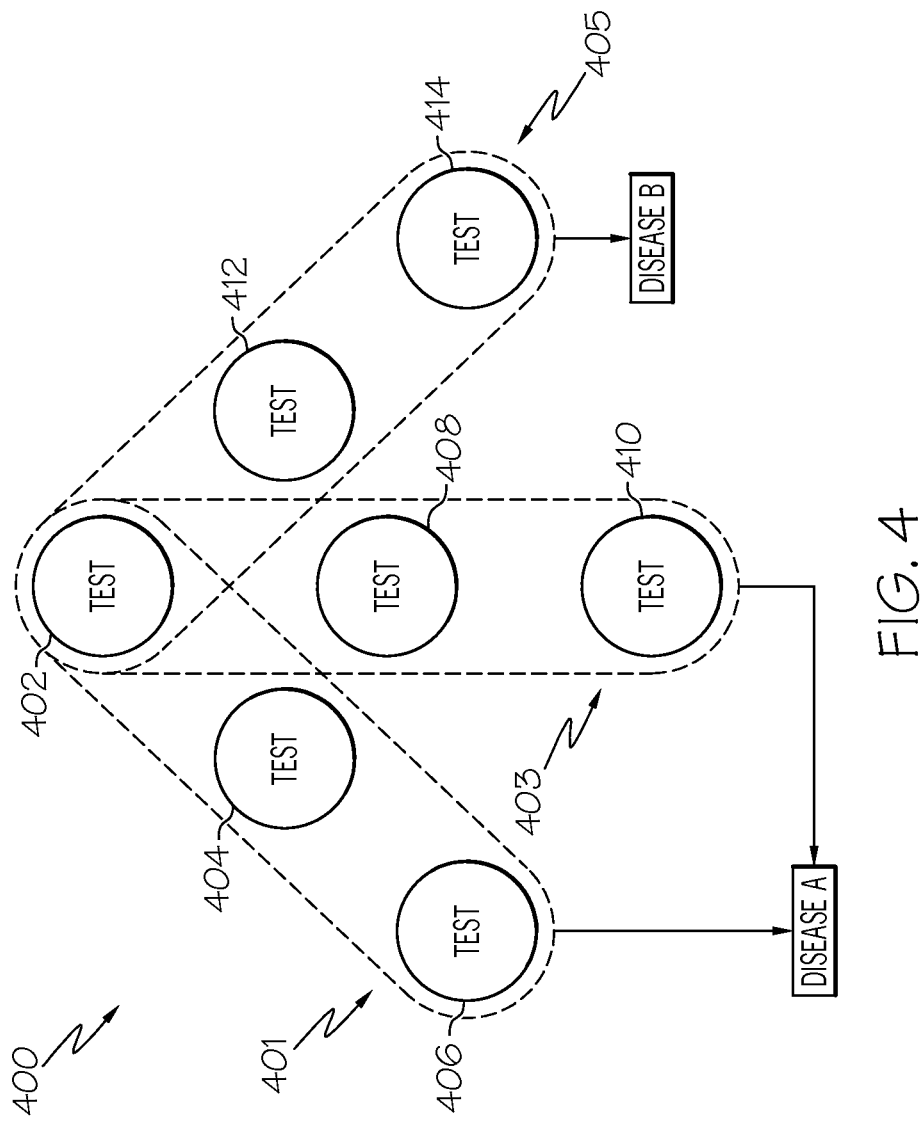
FIG. 4 illustrates exemplary different sets of diagnostic tests used to identify diseases in accordance with one embodiment of the present disclosure.
Figure 5:
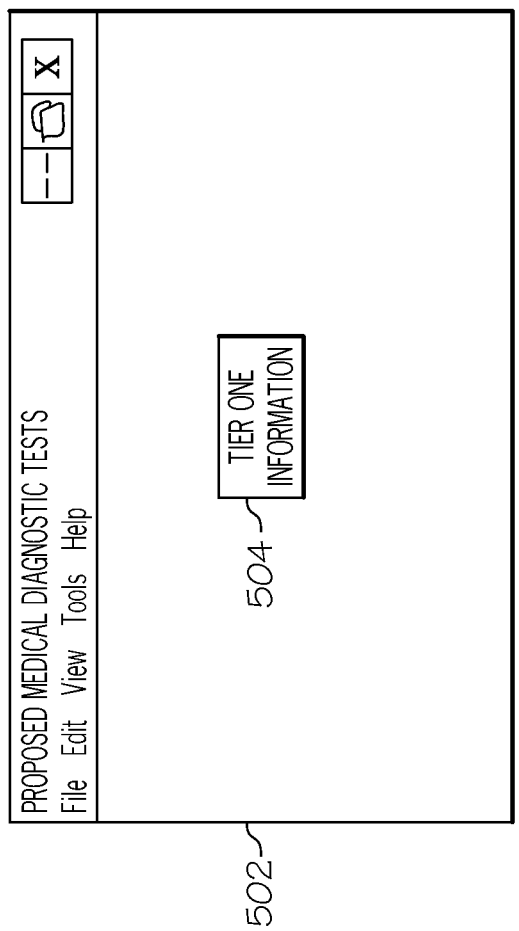
FIG. 5 illustrates an exemplary User Interface (UI) presenting tier one information about suggested diagnostic tests.
Figure 6:
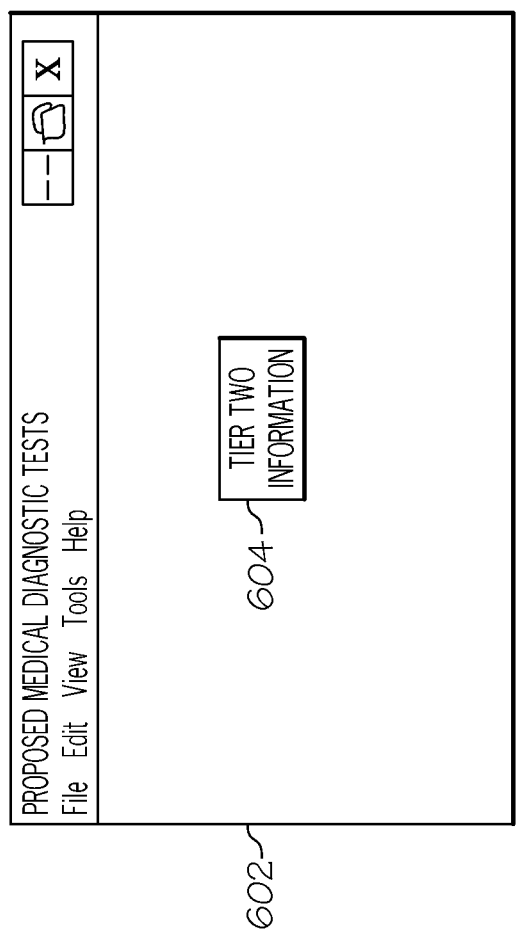
FIG. 6 depicts an exemplary UI presenting tier two information about the same or different suggested diagnostic tests from FIG. 5.

As depicted in FIG. 4, assume that two diagnostic test sets 401 and 403 will each result in the diagnosis of Disease A. Diagnostic test set 401 is made up of diagnostic tests 402, 404, and 406, while diagnostic test set 403 is made up of diagnostic tests 402, 408, and 410. However, assume that the diagnostic tests 408 and 410, either separately or in combination, would inflict a higher level of detrimental effects (pain, cost, delay) on the patient than diagnostic tests 404 and 406. A recommendation would therefore be made to the health care provider to immediately administer diagnostic test 402, since it is the starting test for both diagnostic test sets 401 and 403. Subsequently, a recommendation can be made to administer diagnostic tests 404 and 406, along with the rationale for not recommending the administration of diagnostic tests 408 and 410, to the health care provider. This rationale would include a description of the various detrimental effects that diagnostic tests 408 and 410 may impose on the patient. However, if the test results from diagnostic tests 408 and 410 are deemed significantly more reliable by the health care provider, even when correlated with past cohort experience, then the health care provider may decide to administer these tests anyway.

As depicted by diagnostic test set 405, the diagnosis of another Disease B may also utilize the same diagnostic test 402 used by diagnostic test sets 401 and 403. If the cohort database suggests that the current patient may have either Disease A or Disease B, then the processor would recommend that diagnostic test 402 be administered immediately. However, a recommendation to administer diagnostic tests 412 and/or 414 will subsequently be made only if the detrimental effects of diagnostic tests 412 and/or 414 are deemed to be below a predefined threshold, or if a conclusive diagnosis of Disease A is not made using one of the diagnostic test sets 401 and 403.

Returning to FIG. 2, the sorted (ranked) diagnostic test sets are then presented to a health care provider for the current patient as a recommended set of one or more medical diagnostic tests (block 212). This set of recommendations, and information about the recommended set, can be tailored to the particular health care provider, either as Tier One Information (shown in User Interface (UI) 502 of FIG. 5 in pane 504, or as Tier Two Information (shown in UI 602 of FIG. 6 in pane 604). These two tiers of information may be the same information but with different levels of detail, or they may be different recommended sets of diagnostic tests.

For example, assume that a first health care provider has a low level of education and/or experience when compared to a second health care provider (as identified by a profile of both health care providers that is accessible to a program such as CDDTSP 148 shown in FIG. 1). The Tier Two Information may provide less detailed instructions to the first health care provider as compared to the level of detail provided to the second health care provider. However, assume now that the two health care providers have the same credentials, but one health care provider is situated with the patient inside a health care facility that is able to immediately treat the disease identified by a recommended set of diagnostic tests, while the other health care provider and the patient are hours or days away from such a facility (e.g., due to geographic distance away from the facility, inability to cross a flooded river or snow covered pass to reach the facility, etc.). In such a case, there is no reason to run a set of diagnostic tests that, while faster, may be less accurate. Thus, the temporal proximity of the health care provider and/or the patient to the appropriate health care facility can dictate which diagnostic test set (of one or more tests) is presented to the health care provider.

As shown in block 214 of FIG. 2, once a determination is made that a particular diagnostic test set correctly identifies the disease being suffered by the current patient, the cohort diagnostic test database is updated to reflect this solution. The process ends at terminator block 216.

As described herein, the present invention provides a significant and novel improvement over the prior art. That is, the present invention provides a health care provider with a recommended set of diagnostic tests that are deemed more trustworthy due to the granularity of past histories of cohort patients who have been given the various sets of diagnostic tests. Without the use of the cohort methodology presented herein, the accuracy of a particular diagnostic test will be known only for an entire population, which will be much lower than the accuracy of that diagnostic test for members of the cohort.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of various embodiments of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Note further that any methods described in the present disclosure may be implemented through the use of a VHDL (VHSIC Hardware Description Language) program and a VHDL chip. VHDL is an exemplary design-entry language for Field Programmable Gate Arrays (FPGAs), Application Specific Integrated Circuits (ASICs), and other similar electronic devices. Thus, any software-implemented method described herein may be emulated by a hardware-based VHDL program, which is then applied to a VHDL chip, such as a FPGA.

Having thus described embodiments of the invention of the present application in detail and by reference to illustrative embodiments thereof, it will be apparent that modifications and variations are possible without departing from the scope of the invention defined in the appended claims.

What is claimed is:

1. A method of creating a suggested diagnostic test selection, the method comprising:
   receiving, by one or more processors, a current description of a current patient, wherein the current description comprises a current medical complaint of the current patient, a medical history of the current patient, and a current physical examination result for the current patient;
   defining, by one or more processors, a cohort for the current patient, wherein the cohort comprises persons who have had a same medical complaint, medical history, and physical examination result as the current patient;
   identifying, by one or more processors, past diagnostic test sets used to make correct medical diagnoses for persons in the cohort, wherein the past diagnostic test sets are stored in a cohort diagnostic test database, wherein the current description of the current patient describes two candidate diagnoses for the current patient, wherein two sequential diagnostic test sets from the sorted diagnostic test sets are sets of multiple sequential diagnostic tests, wherein the two sequential diagnostic test sets have a same initial diagnostic test;
   sorting, by one or more processors, the past diagnostic test sets based on increasing levels of a detrimental effect posed by each of the past diagnostic test sets;
   ranking, by one or more processors, the two sequential diagnostic test sets according to levels of detrimental effects posed by executing subsequent diagnostic tests from the two sequential diagnostic test sets after executing the initial diagnostic test;
   recommending, by one or more processors, execution of a lower ranked sequential diagnostic test set only if detrimental effects from executing all of the diagnostic tests in the lower ranked sequential diagnostic test set are below a predetermined level; and
   presenting, by one or more processors, the sorted past diagnostic test sets to a health care provider for the current patient.

2. The method of claim 1, wherein the current description of the current patient further comprises a demographic description of the current patient and a travel history of the current patient, and wherein persons in the cohort further comprise persons having the demographic description of the current patient and the travel history of the current patient.

3. The method of claim 1, wherein the current description of the current patient further comprises a description of an unrelated trauma suffered by the current patient but which is non-attributable to the current medical complaint of the current patient, and wherein persons in the cohort further comprise persons having the unrelated trauma suffered by the persons but which is non-attributable to the current medical complaint of the current patient.

4. The method of claim 1, further comprising:
   determining which of the sorted past diagnostic test sets is a correct diagnostic test set that accurately identifies a medical condition of the current patient; and
   updating the cohort diagnostic test database with the correct diagnostic test set.

5. The method of claim 1, wherein the detrimental effect is a delay in obtaining results from a particular diagnostic test set.

6. The method of claim 1, wherein the detrimental effect is a financial cost incurred from running a particular diagnostic test set.

7. The method of claim 1, wherein the detrimental effect is a level of pain imposed on a patient when running a particular diagnostic test set.

8. The method of claim 1, wherein the detrimental effect is an irreversible condition imposed on a patient when running a particular diagnostic test set.

9. The method of claim 1, further comprising:
modifying, by one or more processors, the presented information about the sorted past diagnostic test sets according to a profile of the health care provider for the current patient, wherein the profile of the health care provider for the current patient is an education level of the health care provider for the current patient.

10. The method of claim 1, further comprising:
modifying, by one or more processors, the presented information about the sorted past diagnostic test sets according to a profile of the health care provider for the current patient, wherein the profile of the health care provider for the current patient is a health care experience level of the health care provider for the current patient.

11. The method of claim 1, further comprising:
modifying, by one or more processors, the presented information about the sorted past diagnostic test sets according to a profile of the health care provider for the current patient, wherein the profile of the health care provider for the current patient is a temporal proximity of the health care provider to a nearest treatment facility that is capable of treating different diseases identified by the sorted past diagnostic test sets.

12. The method of claim 1, wherein at least one of the past diagnostic test sets is a set of one.

13. A computer program product for creating a suggested diagnostic test selection, the computer program product comprising:
a computer readable storage media;
first program instructions to receive a current description of a current patient, wherein the current description comprises a current medical complaint of the current patient, a medical history of the current patient, and a current physical examination result for the current patient;
second program instructions to define a cohort for the current patient, wherein the cohort comprises persons who have had a same medical complaint, medical history, and physical examination result as the current patient;
third program instructions to identify past diagnostic test sets used to make correct medical diagnoses for persons in the cohort, wherein the past diagnostic test sets are stored in a cohort diagnostic test database, wherein the current description of the current patient describes two candidate diagnoses for the current patient, wherein two sequential diagnostic test sets from the sorted diagnostic test sets are sets of multiple sequential diagnostic tests, wherein the two sequential diagnostic test sets have a same initial diagnostic test;
fourth program instructions to sort the past diagnostic test sets based on increasing levels of a detrimental effect posed by each of the past diagnostic test sets;
fifth program instructions to rank the two sequential diagnostic test sets according to levels of detrimental effects posed by executing subsequent diagnostic tests from the two sequential diagnostic test sets after executing the initial diagnostic test;
sixth program instructions to recommend execution of a lower ranked sequential diagnostic test set only if detrimental effects from executing all of the diagnostic tests in the lower ranked sequential diagnostic test set are below a predetermined level; and
seventh program instructions to present the sorted past diagnostic test sets to a health care provider for the current patient;
and wherein the first, second, third, fourth, fifth, sixth, and seventh program instructions are stored on the computer readable storage media.

14. The computer program product of claim 13, wherein the detrimental effect is a delay in obtaining results from a particular diagnostic test set.

15. The computer program product of claim 13, wherein the detrimental effect is a financial cost incurred from running a particular diagnostic test set.

16. The computer program product of claim 13, wherein the detrimental effect is a level of pain imposed on a patient when running a particular diagnostic test set.

17. The computer program product of claim 13, wherein the detrimental effect is an irreversible condition imposed on a patient when running a particular diagnostic test set.

18. The computer program product of claim 13, further comprising:
eighth program instructions to modify the presented information about the sorted past diagnostic test sets according to a profile of the health care provider for the current patient, wherein the profile of the health care provider for the current patient is a temporal proximity of the health care provider to a nearest treatment facility that is capable of treating different diseases identified by the sorted diagnostic test sets; and wherein the eighth program instructions are stored on the computer readable storage media.

19. A computer system comprising:
a processor, a computer readable memory, and a computer readable storage media;
first program instructions to receive a current description of a current patient, wherein the current description comprises a current medical complaint of the current patient, a medical history of the current patient, and a current physical examination result for the current patient;
second program instructions to define a cohort for the current patient, wherein the cohort comprises persons who have had a same medical complaint, medical history, and physical examination result as the current patient;
third program instructions to identify past diagnostic test sets used to make correct medical diagnoses for persons in the cohort, wherein the past diagnostic test sets are stored in a cohort diagnostic test database, wherein the current description of the current patient describes two candidate diagnoses for the current patient, wherein two sequential diagnostic test sets from the sorted diagnostic test sets are sets of multiple sequential diagnostic tests, wherein the two sequential diagnostic test sets have a same initial diagnostic test;
fourth program instructions to sort the past diagnostic test sets based on increasing levels of a detrimental effect posed by each of the past diagnostic test sets;
fifth program instructions to rank the two sequential diagnostic test sets according to levels of detrimental effects posed by executing subsequent diagnostic tests from the two sequential diagnostic test sets after executing the initial diagnostic test;

sixth program instructions to recommend execution of a lower ranked sequential diagnostic test set only if detrimental effects from executing all of the diagnostic tests in the lower ranked sequential diagnostic test set are below a predetermined level; and seventh program instructions to present the sorted past diagnostic test sets to a health care provider for the current patient;

and wherein the first, second, third, fourth, fifth, sixth, and seventh program instructions are stored on the computer readable storage media for execution by the processor via the computer readable memory.

20. The computer system of claim 19, further comprising:

eighth program instructions to modify the presented information about the sorted past diagnostic test sets according to a profile of the health care provider for the current patient, wherein the profile of the health care provider for the current patient is a temporal proximity of the health care provider to a nearest treatment facility that is capable of treating different diseases identified by the sorted diagnostic test sets; and wherein the eighth program instructions are stored on the computer readable storage media for execution by the processor via the computer readable memory.

* * * * *